(12) United States Patent
Fife et al.

(10) Patent No.: US 7,246,626 B2
(45) Date of Patent: Jul. 24, 2007

(54) SANITATION SYSTEM FOR REFRIGERATED FIXTURE HAVING AN AIR CURTAIN

(76) Inventors: Jack Fife, 3852-51 Street, Edmonton, Alberta (CA) T6L 2J7; Brian Smith, 3902-40 Avenue, Leduc, Alberta (CA) T9E 4W3; Garvin Weber, 8410-158 Street, Edmonton, Alberta (CA) T5R 2C4

( * ) Notice: Subject to any disclaimer, the term of this patent is extended or adjusted under 35 U.S.C. 154(b) by 461 days.

(21) Appl. No.: 10/718,841

(22) Filed: Nov. 21, 2003

(65) Prior Publication Data
US 2004/0178282 A1  Sep. 16, 2004

(30) Foreign Application Priority Data
Nov. 21, 2002  (CA)  .................................. 2412244

(51) Int. Cl.
*B08B 3/02*  (2006.01)
(52) U.S. Cl. ............... 134/102.1; 134/104.1; 134/166 R; 422/300
(58) Field of Classification Search ............ 134/104.1, 134/94.1, 99.1, 100.1, 102.1, 166 R; 422/300, 422/302
See application file for complete search history.

(56) References Cited

U.S. PATENT DOCUMENTS

| | | | | |
|---|---|---|---|---|
| 1,950,204 A | * | 3/1934 | Wood et al. ............... | 261/117 |
| 1,995,729 A | * | 3/1935 | Zarotschenzeff ............. | 62/247 |
| 2,038,464 A | * | 4/1936 | Wood ....................... | 211/127.1 |
| 2,531,506 A | * | 11/1950 | Geneck ...................... | 62/247 |
| 3,320,964 A | * | 5/1967 | Tripp ........................ | 134/100.1 |
| 3,499,792 A | * | 3/1970 | Veith ........................ | 134/1 |
| 4,416,120 A | * | 11/1983 | Yono et al. .................. | 62/231 |
| 5,113,881 A | * | 5/1992 | Lin et al. .................... | 134/1 |
| 5,203,180 A | * | 4/1993 | Weisbrich .................... | 62/247 |
| 5,501,241 A | * | 3/1996 | Jacobson .................... | 134/95.2 |

FOREIGN PATENT DOCUMENTS

| | | | |
|---|---|---|---|
| GB | 2 319 330 | * | 5/1996 |
| GB | 2 301 175 | * | 11/1996 |
| GB | 2 317 688 | * | 4/1998 |
| GB | 2 326 095 | * | 12/1998 |
| JP | 11-290049 | * | 10/1999 |
| JP | 2000-220949 | * | 8/2000 |
| KR | 2002029014 | * | 4/2002 |

* cited by examiner

*Primary Examiner*—Frankie L. Stinson
(74) *Attorney, Agent, or Firm*—Davis, Bujold & Daniels, P.L.L.C.

(57) ABSTRACT

A sanitation system for a refrigerated fixture having an air curtain. This sanitation includes a spray manifold positioned in a case tank of the refrigerated fixture. A reservoir is provided which is adapted to contain disinfectant. A pump is provided to pump disinfectant from the reservoir through the spray manifold, whereby disinfectant is sprayed into the case tank. A controller is connected to the pump and adapted to control the frequency and duration of the spray through the spray manifold.

9 Claims, 3 Drawing Sheets

SANITATION SYSTEM FOR REFRIGERATED FIXTURE HAVING AN AIR CURTAIN

FIELD OF THE INVENTION

The present invention relates to a sanitation system for a refrigerated fixture having an air curtain.

BACKGROUND OF THE INVENTION

A refrigerated fixture has a product support positioned over a recessed area, referred to as a "case tank". An air curtain is used to maintain product positioned on the product support within a required temperature range, often referred to as a "core temperature" or "critical air temperature". The air curtain keeps out ambient air that would raise the product temperature and has little or no discharge of cool air into the room.

The air curtain has a circular circulation of air. Cool air exiting a refrigeration unit is discharged onto a first side of the product support and flows across the product to a second side of the product support. A return air duct is positioned at the second side of the product support and a fan is positioned within the case tank. The fan draws air through the return air duct and directs the air back into the refrigeration unit.

With some types of product, such as fruit and vegetables, water misters operated on timers are used to moisten the product. With other types of product, such as seafood and red meat, the product has natural juices that drip through the product support and into the case tank. As a result, the case tank tends to be a cool, damp and dark environment. Unfortunately many bacteria, such as *Pseudomonas aeruginosa*, salmonella, staphylococcus, black mould, *E. Coli*, streptococcus, and the like, thrive in a cool, damp and dark environment. A bacteria concentration of as little as one to six parts per million can cause illness in humans. Should the case tank become contaminated, the air circulation of the air curtain will repeatedly pass contaminated air over the product until the product on display is thoroughly contaminated. The sanitizing of the case tank of a refrigerated fixture is, therefore, of vital importance. Periodic cleaning by store personnel is inadequate to address the dangers of contamination of refrigerated fixtures by *Pseudomonas aeruginosa*, salmonella, staphylococcus, black mould, *E. Coli*, streptococcus, and the like.

SUMMARY OF THE INVENTION

What is required is an effective sanitation system for refrigerated fixtures.

According to the present invention there is provided a sanitation system for a refrigerated fixture. This sanitation includes a spray manifold positioned in a case tank of the refrigerated fixture. A reservoir is provided which is adapted to contain disinfectant. A pump is provided adapted to pump disinfectant from the reservoir through the spray manifold, whereby disinfectant is sprayed into the case tank. A controller is connected to the pump and adapted to control the frequency and duration of the spray through the spray manifold.

The most effective disinfectant tested appears to be a quaternary ammonium. This disinfectant is effective in concentrations of 200 parts per million. Even more beneficial results may, therefore, be obtained when water is supplied to the pump as a diluent via a water supply line and a metering valve is used to combine desired proportions of water and disinfectant.

A calcium build-up can, over time, adversely affect the functioning of the sanitation system. Even more beneficial results may, therefore, be obtained when a filter is provided on the water supply line to filter out contaminants.

Any form of backflow in the system would be counter-productive. It is undesirable to have a backflow of disinfectant into the water system. Even more beneficial results may, therefore, be obtained when a one way valve is positioned on the water supply line to prevent backflow. A backflow into the reservoir would stop the proper proportions of disinfectant and water being mixed. Even more beneficial results may, therefore, be obtained when a one way valve is disposed between the reservoir and the pump to prevent backflow.

It is envisaged that the reservoir, pump, and controller will all be positioned on a single panel. The panel can then be installed in a convenient location near the refrigerated fixture and feed lines run to the spray manifold within the case tank.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
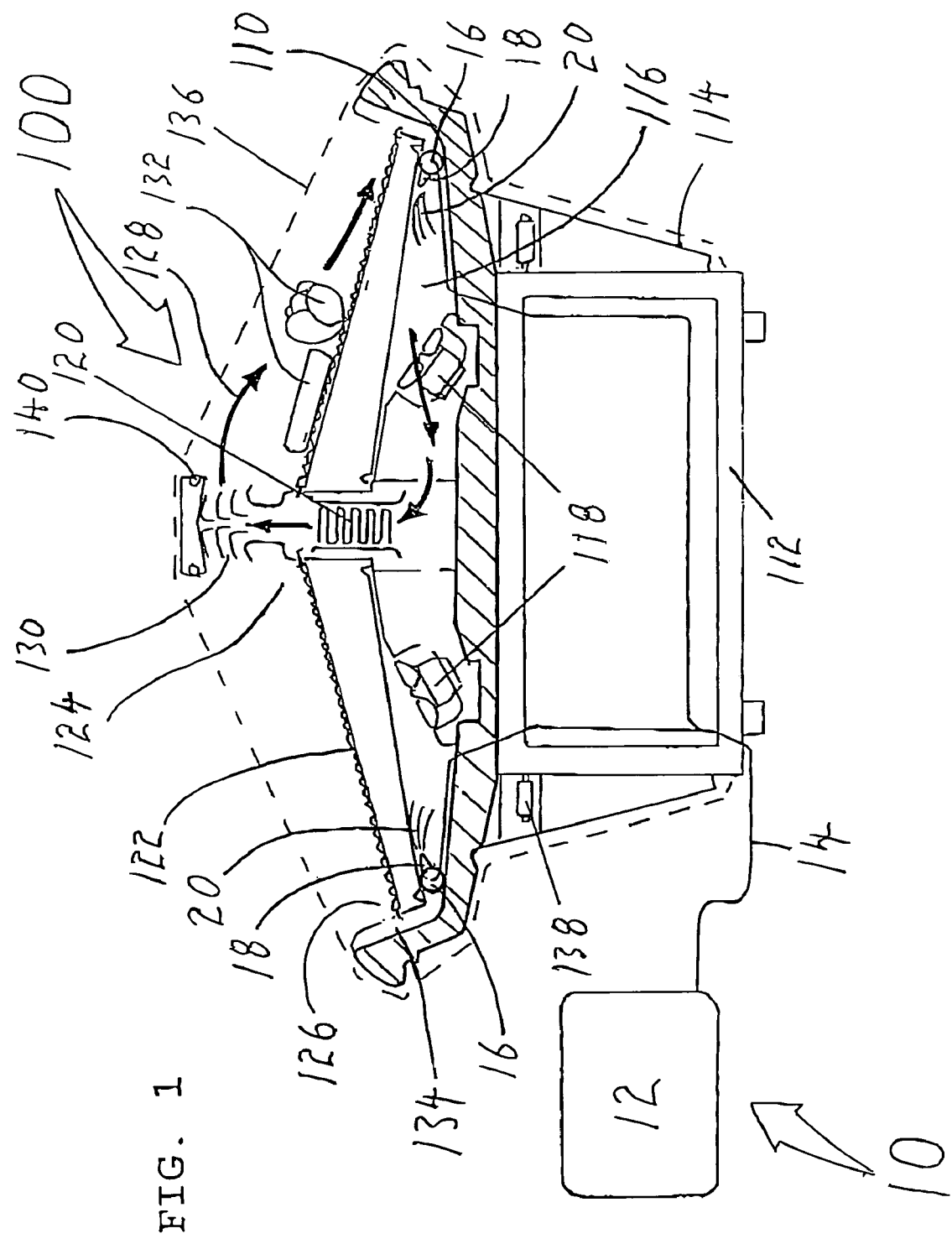
FIG. 1 is an end elevation view of a refrigerated fixture equipped with a sanitation system constructed in accordance with the teachings of the present invention.

The preferred embodiment, a sanitation system generally identified by reference numeral 10, will now be described with reference to FIGS. 1 and 2.

Figure 2:
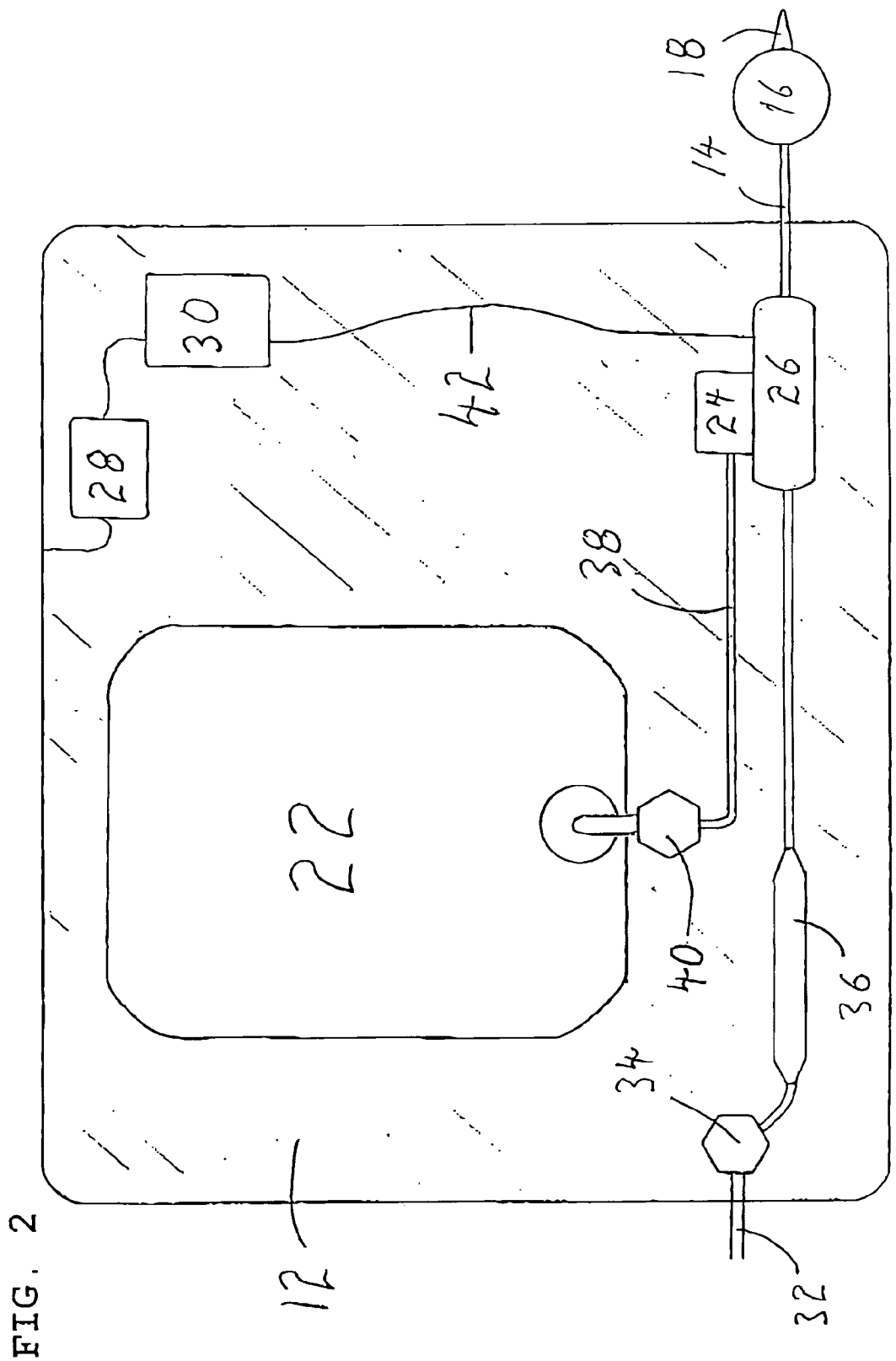
FIG. 2 is a detailed front elevation view of a panel containing components of the sanitation system illustrated in FIG. 1.

Structure and Relationship of Parts:

Referring to FIG. 1, sanitation system 10 was developed for use with a refrigerated fixture, generally indicated by reference numeral 100. Refrigerated fixture 100 consists of a body 110, base 112 and outer shell 114. Body 110 has a case tank 116 with fans 118 and a refrigeration unit 120. Refrigerated fixture 100 is further adapted with product support 122 having a first side 124 and a second side 126. Fans 118 create air circulation 128 that passes through refrigeration unit 120 and out cool air discharge vents 130. Air circulation 128 then passes from first side 124 over product 132 to second side 126 and ultimately through return air ducts 134. This air circulation forms an air curtain 136 over product 132. Refrigeration fixture 100 may be further adapted with water accessory 138 and water misters 140.

Sanitation system 10 has panel 12 with feed lines 14 connecting to spray manifolds 16. Spray manifolds 16 are adapted with nozzles 18 which effect spray 20. Referring to FIG. 2, the following components are positioned on panel 12: a reservoir 22 adapted to contain disinfectant, a metering valve 24 and a pump 26 adapted to meter and pump disinfectant. A transformer 28 is provided which is adapted to regulate voltage and a controller 30 is provided which is adapted to control frequency and duration of disbursal of disinfectant. A water supply line 32 passes through a one way valve 34 and a filter 36 and connects to pump 26. A disinfectant supply line 38 passes through a second one way valve 40 and connects to metering valve 24. Wiring harness 42 connects transformer 28 and controller 30 to pump 26. Feed line 14 connects pump 26 to spray manifold 16 and nozzles 18.

Operation:

The use and operation of a sanitation system 10 will now be described with reference to FIGS. 1 and 2. Referring to FIG. 2, water is supplied through water supply line 32 and passes through first one way valve 34. One way valve 34 prevents water from reversing flow and permitting disinfectant to pass into the municipal water system. Water proceeds through filter 36 to reduce calcium build-up within the system. Disinfectant is drawn from reservoir 22 through second one way valve 40. Second one way valve 40 also prevents water disrupting the flow of disinfectant. Power is regulated and controlled by transformer 28. Controller 30 intermittently activates pump 26 according to a programmed schedule relating to frequency and duration of disinfectant. As water and disinfectant are pumped through metering valve 24, metering valve 24 determines the ratio of disinfectant to water and the resultant mix is transported through feed lines 14 to spray manifolds 16. Nozzles 18, when spaced along spray manifold 16 disperse an effective amount of disinfectant within case tank 116 such that virtually all bacteria in case tank 116 is killed.

Variations:

Although a refrigeration system having an air curtain has been chosen for purposes of illustration, it will be appreciated that the invention can be used with other types of refrigeration fixtures.

Figure 3:
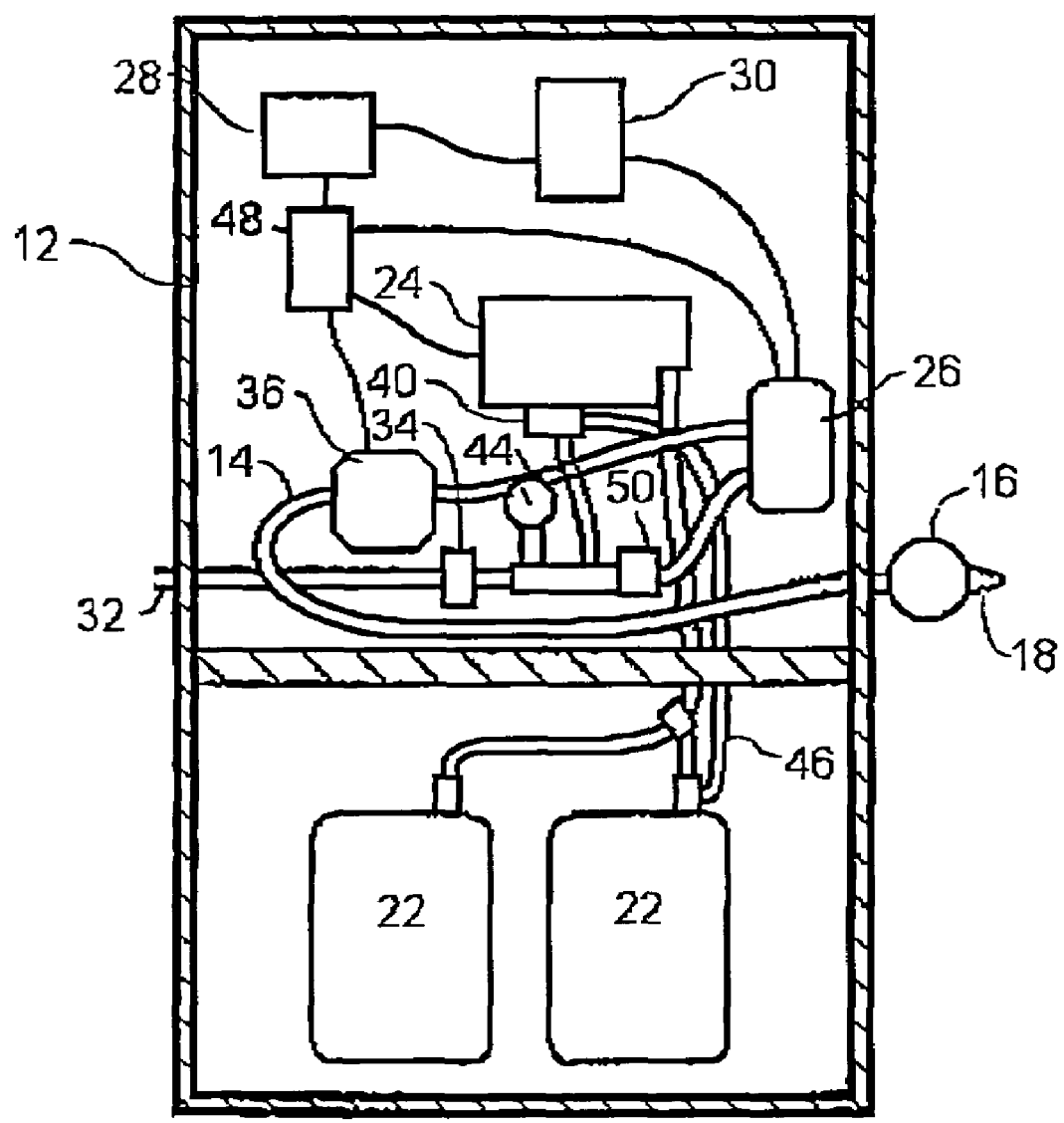
FIG. 3 is a detailed front elevation view of an alternate panel containing components of the sanitation system illustrated in FIG. 1.

Referring to FIG. 3, an alternate embodiment of the panel is shown. This embodiment generally follows the same operation as that shown in FIG. 2 and described above, where like reference numerals refer to like elements. The transformer 28, metering valve 24, filter 36, and pump 26 are all powered by power source 48. Water enters the panel 12 through line 32, passes through the one way valve 34, and then passes through a pressure valve 44. The disinfectant is drawn from one of two reservoirs 22, through the metering valve 24 and one way valve 40, and enters the water flow after the pressure valve 44. There is also an overflow line 46 connected to one way valve 40, which return any excess disinfectant to the reservoir 22. The water and disinfectant mixture then passes through a flow regulator 50. Pump 26 pumps the mixture through filter 36 to spray manifolds 16 and out nozzles 18.

This alternative control panel provides a number of advantages. With the original control panel, variations in water pressure changed the vacuum pressure and resulted in variations in chemical input. With the alternative control panel, flow regulator 50 keeps the flow constant and metering valve 24 ensures a consistent input of disinfectant. The use of two five gallon reservoirs allows the system to operate for longer periods between servicing.

Cautionary Warnings:

It is preferred that the disinfectant selected must be capable of providing a 100% kill rate. In tests the best disinfectant of those tested was quaternary ammonium. Quaternary ammonium in concentrations of 200 parts per million had a 100% kill rate. However, quaternary ammonium had some undesirable side effects. It adversely affects some types of plastics. Care should be taken when using plastic components, such as plastic valves. The spray manifold should be arranged to provide thorough spray coverage within the case tank. This was achieve by placing nozzles every 12 inches and using a swirling spray pattern. It will be appreciated that with further testing effective anti-bacterial solutions may be found that do not have the undesirable side effects inherent with quaternary ammonium.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. In combination:
    a refrigerated fixture having a case tank, a product support supported by the case tank and a moisturizing spray manifold positioned above the product support which sprays liquid onto the product support to maintain moisture in produce displayed on the product support:
    a sanitation system for the refrigerated fixture, comprising:
        a disinfecting spray manifold positioned in the case tank of the refrigerated fixture below the product support, the disinfecting spray manifold being arranged to provide thorough spray coverage in a swirling spray pattern within the case tank without adversely affecting the produce concurrently on display on the product support;
        a reservoir adapted to contain a chemical disinfectant that kills bacteria on contact;
        a pump adapted to pump disinfectant from the reservoir through the disinfecting spray manifold, whereby disinfectant is sprayed into the case tank;
        a controller connected to the pump and adapted to control the frequency and duration of the spray through the disinfecting spray manifold.

2. The sanitation system as defined in claim 1, wherein the disinfectant is a quaternary ammonium.

3. The sanitation system as defined in claim 1, wherein water is supplied to the pump via a water supply line and a metering valve is used to combine desired proportions of water and disinfectant.

4. The sanitation system as defined in claim 3, wherein a filter is provided on the water supply line to filter out contaminants.

5. The sanitation system as defined in claim 1, wherein a one way valve is positioned on the water supply line to prevent backflow.

6. The sanitation system as defined in claim 1, wherein a one way valve is disposed between the reservoir and the pump to prevent backflow.

7. The sanitation system as defined in claim 1, wherein the pump and the controller are positioned on a panel.

8. The sanitation system as defined in claim 1, wherein a flow regulator is used to maintain a constant flow rate.

9. The sanitation system as defined in claim 1, wherein a metering valve is used to ensure a consistent injection of disinfectant.

* * * * *